(12) United States Patent
Young et al.

(10) Patent No.: US 12,390,133 B2
(45) Date of Patent: Aug. 19, 2025

(54) SENSOR ASSEMBLY APPARATUS AND METHODS FOR CONTINUOUS GLUCOSE MONITORS

(71) Applicant: Ascensia Diabetes Care Holdings AG, Basel (CH)

(72) Inventors: Cameron M. Young, San Diego, CA (US); Jennifer L. Gass, Tarrytown, NY (US); Thomas A. J. Mayer, Jr., Glenmore, PA (US); Eugene Prais, West Milford, NJ (US)

(73) Assignee: Ascenia Diabetes Care Holdings AG, Basel (CH)

( * ) Notice: Subject to any disclaimer, the term of this patent is extended or adjusted under 35 U.S.C. 154(b) by 42 days.

(21) Appl. No.: 18/330,971

(22) Filed: Jun. 7, 2023

(65) Prior Publication Data

US 2023/0309867 A1    Oct. 5, 2023

Related U.S. Application Data

(63) Continuation of application No. 16/382,189, filed on Apr. 11, 2019, now Pat. No. 11,751,778.

(Continued)

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/686* (2013.01)

(58) Field of Classification Search
CPC ............ A61B 5/14532; A61B 5/14503; A61B 5/14546; A61B 5/1411; A61B 5/150022;

(Continued)

(56) References Cited

U.S. PATENT DOCUMENTS

2008/0027296 A1    1/2008  Hadvary et al.
2013/0150691 A1*   6/2013  Pace ............... A61B 5/150305
                                                    600/347

(Continued)

FOREIGN PATENT DOCUMENTS

CN    107106090 A    8/2017
EP      3202323 A1   8/2017
JP    2015509011 A   3/2015

OTHER PUBLICATIONS

Chinese Patent Application 201980031347.3 Second Office Action issued Nov. 30, 2023.

(Continued)

*Primary Examiner* — Jennifer Robertson
*Assistant Examiner* — Karen E Toth
(74) *Attorney, Agent, or Firm* — Erise IP, P.A.

(57) ABSTRACT

A sensor apparatus for a continuous glucose monitoring system has a sensor housing that includes a first end having a sealing surface configured to seal against an introducer having an insertion shaft, a second end having a sealing surface configured to seal against an insertion shaft cover, and an insertion shaft opening having a width that allows the insertion shaft to travel there through and that extends between the first and second ends. The sensor housing may further include a sensor wire channel that extends between the insertion shaft opening and a sensor wire contact location in an outer surface of the sensor housing. The sensor wire channel and sensor wire contact location may be configured to receive a sensor that extends between the insertion shaft opening and the sensor wire contact location to allow the sensor to make electrical contact to system circuitry. Numerous other aspects are provided.

10 Claims, 8 Drawing Sheets

Related U.S. Application Data (60) Provisional application No. 62/657,612, filed on Apr. 13, 2018.

(58) Field of Classification Search
CPC ..... A61B 5/145; A61B 5/1451; A61B 5/1459; A61B 5/1486; A61B 5/14865
See application file for complete search history.

(56) References Cited

U.S. PATENT DOCUMENTS

| | | |
|---|---|---|
| 2014/0066730 A1 | 3/2014 | Roesicke et al. |
| 2015/0018639 A1 | 1/2015 | Stafford |
| 2017/0188912 A1* | 7/2017 | Halac ..................... A61B 5/688 |

OTHER PUBLICATIONS

Chinese Application 201980031347.3 First Office Action and Search Report issued May 6, 2023.
Chinese Patent Application Notification of Granting Invention Patent Right issued Mar. 22, 2024.
European Patent Application 19718294.2 Office Action issued Jan. 30, 2024.

* cited by examiner

SENSOR ASSEMBLY APPARATUS AND METHODS FOR CONTINUOUS GLUCOSE MONITORS

CROSS-REFERENCE TO RELATED APPLICATIONS

This application claims the benefit of U.S. patent application Ser. No. 16/382,189, filed Apr. 11, 2019, which claims the benefit of U.S. Provisional Patent Application No. 62/657,612, filed Apr. 13, 2018, which are both hereby incorporated herein by reference in their entirety for all purposes.

FIELD

The present disclosure relates generally to continuous glucose monitoring (CGM) and more particularly to apparatus and methods for sensor assemblies for CGMs.

BACKGROUND

Existing CGM products provide frequent measurements of a patient's glucose levels without the need for each such measurement to be accompanied by the drawing of blood, such as by "finger sticks." CGM products may include a sensor portion that is inserted so as to be located under the skin, and a processing portion that is adhered to the outer surface of the skin, for example, the abdomen or back of the upper arm. These CGM products are worn for a number of days before being removed and replaced.

The sensor that has been inserted under the skin provides a signal to the processing portion of the CGM product, and that signal is indicative of the patient's blood glucose level. These measurements may be made automatically many times throughout the day (e.g., every 5 minutes or at some other interval).

The processing portion of a CGM product may include electrical circuitry for interpreting the signal provided by the sensor, and for storing and/or communicating information regarding the patient's blood glucose levels.

SUMMARY

In one example embodiment, a sensor apparatus, including a sensor housing, for a continuous glucose monitoring system is provided. The sensor housing includes a first end having a sealing surface configured to seal against an introducer having an insertion shaft, a second end having a sealing surface configured to seal against an insertion shaft cover, and an insertion shaft opening having a width that allows the insertion shaft of the introducer to travel through the insertion shaft opening, and that extends between the first end and the second end. The insertion shaft opening defines an inner surface of the sensor housing. The sensor housing also has an outer surface with a sensor wire contact location. The sensor housing may further include a sensor wire channel that extends between the insertion shaft opening of the sensor housing and the sensor wire contact location. In this example embodiment, the sensor wire channel and sensor wire contact location may be configured to receive a sensor that extends between the insertion shaft opening of the sensor housing and the sensor wire contact location, and may be further configured to allow the sensor to make electrical contact to circuitry of the continuous glucose monitoring system.

In another example embodiment, a sensor assembly for a continuous glucose monitoring system is provided. The sensor assembly includes an introducer having an insertion shaft, an insertion shaft cover surrounding a portion of the insertion shaft, a sensor having a first end and a second end, the first end of the sensor positioned within the insertion shaft, and a sensor housing. The sensor housing may include a first end having a sealing surface configured to seal against the introducer, and a second end having a sealing surface configured to seal against the insertion shaft cover. The sensor housing may further include an insertion shaft opening that extends between the first end and the second end, the insertion shaft opening having a width that allows the insertion shaft to travel through the opening, and the insertion shaft opening defines an inner surface of the sensor housing. The sensor housing may still further include an outer surface having a sensor wire contact location, and a sensor wire channel that extends between the insertion shaft opening of the sensor housing and the sensor wire contact location, wherein the sensor extends between the insertion shaft opening of the sensor housing and the sensor wire contact location. The sensor assembly may further include a receiving surface having a receiving area, and a sensor housing support. The sensor housing support may include an outer surface, an inner surface, and a vertical contact element channel extending between the outer surface and the inner surface. The sensor assembly may still further include a substrate such as a circuit board having electrical circuitry for the continuous glucose monitoring system coupled thereto. In various embodiments, one or more components of the electrical circuitry may be mounted on the substrate, and/or one or more components of the electrical circuitry may be coupled to the substrate, such as by a corresponding one or more sockets. It will be appreciated that sockets may be physically attached to the substrate, and components, such as but not limited to integrated circuits, may be inserted into the sockets that provide mechanical support for the components, and further provide electrical connection between the electrical components and one or more electrically conductive traces on the substrate. In this example embodiment, the substrate is positioned within the receiving area of the receiving surface. A vertical contact element may be provided and positioned within the vertical contact element channel of the sensor housing support of the receiving surface. The vertical contact element may be in electrical contact with the electrical circuitry. The sensor housing is positioned within the sensor housing support of the receiving surface, and the vertical contact element and the sensor are in electrical contact at the sensor wire contact location such that the sensor is in electrical contact with the electrical circuitry.

In some embodiments, a method of assembling a sensor assembly for a continuous glucose monitoring system is provided. The method includes (1) providing a sensor housing including (a) a first end having a sealing surface configured to seal against an introducer; (b) a second end having a sealing surface configured to seal against an insertion shaft cover; (c) an insertion shaft opening that extends between the first end and the second end and having a width that allows at least a portion of an insertion shaft of the introducer to travel through the insertion shaft opening, the insertion shaft opening defining an inner surface of the sensor housing; (d) an outer surface having a sensor wire contact location; and (e) a sensor wire channel that extends between the inner surface of the insertion shaft opening of the sensor housing and the sensor wire contact location. The method further includes (2) installing a sensor so that the sensor extends between the insertion shaft opening of the sensor housing and the sensor wire contact location of the sensor housing; (3) installing an insertion shaft through the first end of the sensor housing; (4) coupling an insertion shaft cover to the second end of the sensor housing; (5) providing a receiving surface having a receiving area and a sensor housing support, the sensor housing support including an outer surface, an inner surface, and a vertical contact element channel extending between the outer surface and inner surfaces; (6) installing a substrate having electrical circuitry coupled thereto for the continuous glucose monitoring system in the receiving area of the receiving surface; (7) installing a vertical contact element within the vertical contact element channel of the sensor housing support of the receiving surface such that the vertical contact element is in electrical contact with the electrical circuitry; and (8) installing the sensor housing within the sensor housing support of the receiving surface so that the vertical contact element and the sensor are in electrical contact at the sensor wire contact location, and the sensor is in electrical contact with the electrical circuitry.

Other features, aspects, and advantages of embodiments in accordance with the present disclosure will become more fully apparent from the following detailed description, the subjoined claims, and the accompanying drawings by illustrating a number of example embodiments and implementations. Various embodiments in accordance with the present disclosure may also be capable of other and different applications, and its several details may be modified in various respects, all without departing from the scope of the claims. Accordingly, the drawings and descriptions are to be regarded as illustrative in nature, and not as restrictive. The drawings are not necessarily drawn to scale.

BRIEF DESCRIPTION OF THE DRAWINGS

FIG. 6C is similar to FIG. 1B, but with the insertion shaft and insertion shaft cover of FIG. 1B removed so as to provide an additional illustration of the relation between the top case, bottom case, substrate, sensor housing, and sensor (e.g., when the sensor assembly is adhered to the skin of a user).

DETAILED DESCRIPTION

Embodiments of the present invention allow formation of a module having a sensor and an insertion shaft of an introducer that may be separately sterilized and then easily and securely connected to an electronic circuit of a continuous glucose monitor during assembly. Vertically oriented interconnections between the sensor and the electronic circuit reduce overall footprint of the monitor.

In order to perform continuous glucose monitoring, a sensor is inserted into a patient and electrical circuitry is coupled to the sensor. The electrical circuitry may be used for processing information obtained from the sensor, and transmitting information to one or more external devices used by patients and/or healthcare providers to, among other things, track the patient's blood glucose level over time. A housing containing the electrical circuitry is adhered to the patient's skin with the sensor extending into the patient, and remains on the patient's skin for several days (e.g., up to a week or more in some cases).

Because the housing containing the electrical circuitry remains on the patient's skin, it is desirable to make the housing comfortable for the patient, easy to adhere, and securely attachable. Reducing the size of the housing may achieve these goals, as a smaller device is easier to secure to the patient, is more comfortable, and is less likely to become detached (e.g., by becoming snagged on clothing or otherwise bumped or displaced).

Various embodiments in accordance with the present disclosure provide a vertically oriented electrical connection between a sensor of a continuous glucose monitor and the electrical circuitry of the monitor. Conventionally, such a connection is made laterally (coplanarly) on the substrate on which the monitor's electrical circuitry is mounted. By orienting the electrical connection vertically, more space is provided for the monitor's electrical circuitry and the overall footprint of the monitor's housing may be reduced. A reduced footprint housing may provide for a more comfortable continuous glucose monitor that is easy to attach securely to a patient's skin. A smaller-sized monitor also is more discrete which may be favorable to many users.

In addition, in one or more embodiments provided herein, portions of a continuous glucose monitor may be sterilized separately and/or using different sterilization processes. For example, in one or more embodiments, the sensor and insertion shaft of a continuous glucose monitor may be isolated from and/or separately sterilizable from the electrical circuitry of the continuous glucose monitor. Such an arrangement allows the sensor and insertion shaft to be sterilized using a first process, such as an electron beam, gamma beam, or similar process, while the electrical circuitry may be sterilized using a second process, such as a chemical or similar process. Electron or gamma beam sterilization is effective for sterilizing sensors and insertion shafts without damaging the enzymes used by the sensors for glucose detection. However, electron or gamma beam sterilization may damage sensitive electrical circuitry. Likewise, chemical sterilization, using ethylene oxide or another chemical, is effective at sterilizing electrical circuitry and the substrate on which the electrical circuitry is mounted without damaging these components. However, chemical sterilization may destroy the enzymes used by sensors for glucose detection. Therefore, providing a configuration that allows the sensor and insertion shaft to be sterilized separately from the electrical circuitry of a continuous glucose monitor provides additional benefits.

These and other embodiments of the present disclosure are described below with reference to FIGS. 1A-9.

Figure 1A:
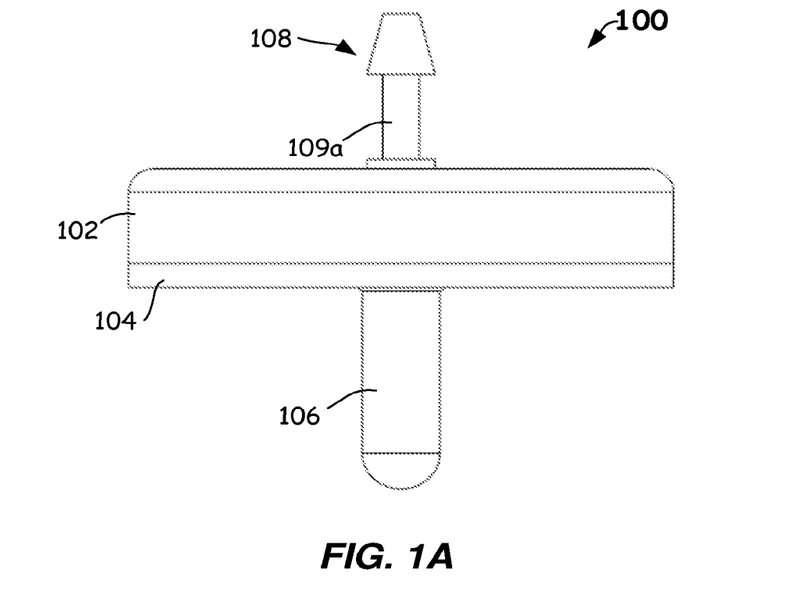
FIG. 1A illustrates a side view of a sensor housing module in accordance with an example embodiment of the disclosure.

FIG. 1A illustrates a side view of an example sensor housing module 100 in accordance with an example embodiment of the disclosure. Example sensor housing module 100 includes a top case 102, and a receiving surface such as a bottom case 104 attached to top case 102. Example sensor housing module 100 further includes an insertion shaft cover 106 extending outwardly from bottom case 104, and an introducer 108, a handle portion 109a which extends outwardly from top case 102. Introducer 108 may include an insertion shaft 109b (FIG. 1B) such as a hollow cylinder with a sharply pointed end used to introduce a sensor into a patient's interstitial fluid. In this example embodiment, introducer 108 may be used to insert a sensor into a patient such that the sensor, or at least a portion of the sensor, is located under the patient's skin.

In some embodiments, top case 102, bottom case 104, insertion shaft cover 106, and/or the introducer's handle portion 109a may be made from one or more materials, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE).

In some embodiments the insertion shaft 109b of introducer 108 may be made from a metal such as stainless steel. In some embodiments the insertion shaft 109b of introducer 108 may be made from one or more materials such as, but not limited to, plastic. In some embodiments, insertion shaft 109b of introducer 108 is insert-molded with a plastic handle portion 109a, and insertion shaft 109b of introducer 108 may be, but is not limited to, a round C-channel tube, a round U-channel tube, a stamped sheet metal part folded into a square U-profile, a molded/cast metal part with a square U-channel profile, or a solid metal cylinder with an etched or ground square U-channel. In some example embodiments, for insertion shaft 109b of introducer 108 implemented as a C-channel or U-channel tube insertion shaft, the tube may have an inner diameter in the range of 400 μm to 700 μm and a thickness in the range of 100 μm to 250 μm. In some example embodiments, for insertion shaft 109b of introducer 108 implemented as stamped sheet metal folded into a square U-profile, the inner width and height may be in a range from 400 μm to 700 μm, with a wall thickness in a range from 100 μm to 250 μm. In some example embodiments, for insertion shaft 109b of introducer 108 implemented as a molded or cast metal part, the outer diameter of the insertion shaft 109b may be in the range of 1200 μm to 2000 μm, and inner channel of the insertion shaft 109b may have a width and height between 400 μm to 700 μm. In some example embodiments, the length of introducer 108 including the handle portion 109a and insertion shaft 109b may be approximately 18 mm to 22 mm, and the length of insertion shaft 109b of introducer 108 may be approximately 12 mm to 15 mm. Other introducer and/or insertion shaft configurations, sizes, and/or materials may be used.

Figure 1B:
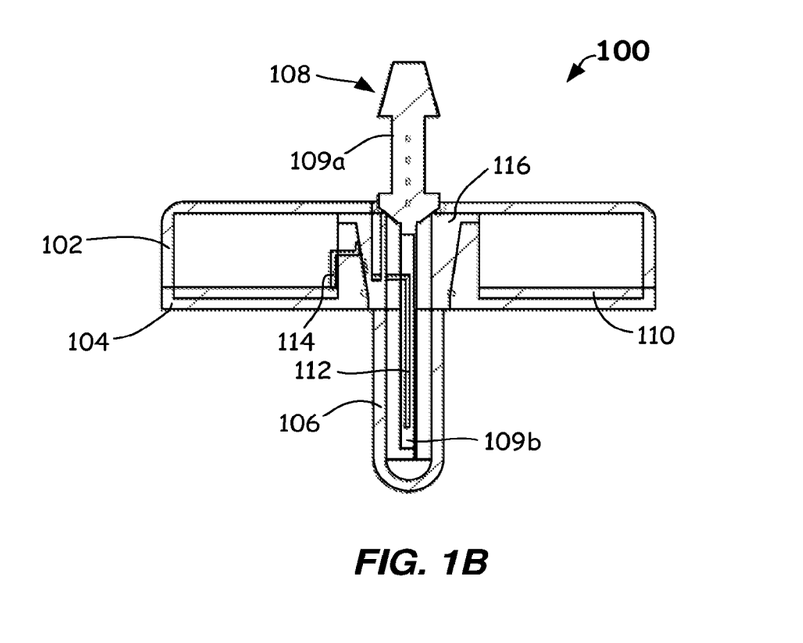
FIG. 1B illustrates a cross-sectional view of the sensor housing module of FIG. 1A in accordance with an example embodiment of the disclosure.

FIG. 1B illustrates a cross-sectional view of the sensor housing module 100 of FIG. 1A in accordance with an example embodiment of the disclosure. A substrate 110, such as a printed circuit board, is shown disposed on an inner surface of bottom case 104. In some example embodiments, substrate 110 may have a thickness in a range of, but not limited to, about 0.6 mm to 0.8 mm. In one or more embodiments, substrate 110 may be, for example, a 4-layer printed circuit board. Substrate 110 may be electrically non-conductive, and may have electrically conductive traces formed thereon and therein. Other printed circuit board configurations, sizes and/or materials may be employed.

In accordance with the example embodiment illustrated in FIG. 1B, sensor 112 is shown extending into a region defined by the inner surface of insertion shaft cover 106.

A vertical contact element 114 is shown in contact with substrate 110 and further in contact with an outer sidewall portion of a sensor housing 116. It will be appreciated that vertical contact element 114 may be in contact with an electrically conductive material disposed on substrate 110, rather than directly upon an electrically non-conductive portion of substrate 110. In various embodiments, vertical contact element 114 may be made from high grade stainless steel, solid silver, gold, or copper with a silver/gold/stainless steel plating or any other suitable conductive material. In still further embodiments, vertical contact element 114 may be made from a combination of carbon rubber and solid gold/silver or a similar material to provide a non-bimetal contact. While one vertical contact element 114 is shown in FIG. 1B, in some embodiments, multiple vertical contact elements may extend from substrate 110 as described further below (e.g., 2, 3, or more vertical contact elements).

In some embodiments sensor housing 116 may be made from one or more materials, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE).

Figure 2A:
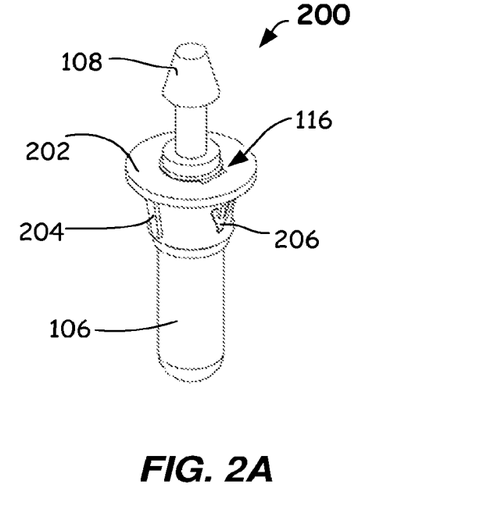
FIG. 2A illustrates a sensor housing assembly in accordance with an example embodiment of the disclosure.

FIG. 2A illustrates a sensor housing assembly 200 in accordance with an example embodiment of the disclosure. Example sensor housing assembly 200 includes sensor housing 116, which has an upper external surface 202, an alignment feature 204 disposed at a first location on an outer sidewall of sensor housing 116 and that extends outwardly therefrom, and a sensor wire contact location 206 disposed at a second location on the outer sidewall of sensor housing 116. The sensor wire contact location 206 may be, for example, a surface, an opening and/or recess in the outer sidewall of sensor housing 116, and any sensor positioned therein may be recessed below, level with or protruding from the outer sidewall of the sensor housing 116. It will be appreciated that more than one alignment feature 204 may be disposed at various outer sidewall locations of sensor housing 116 (e.g., alignment feature 204 shown in FIG. 2A and alignment feature 204 shown in FIG. 2C). Alignment feature 204 facilitates assembly of sensor housing module 100 by fixing an orientation of sensor housing 116 relative to bottom case 104 (as described in greater detail below). Sensor wire contact location 206 provides a region in the outer surface of sensor housing 116 for placement of a sensor (as described below).

Figure 2B:
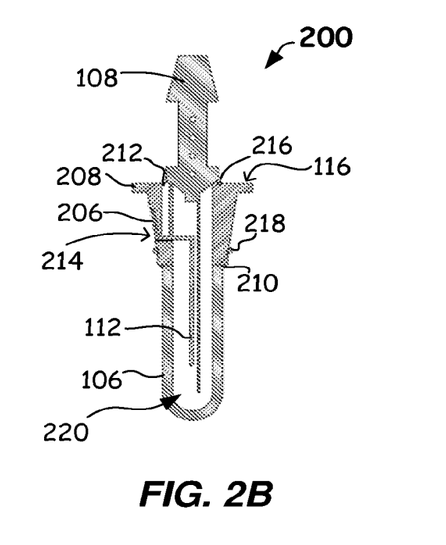
FIG. 2B illustrates a cross-sectional view of the sensor housing assembly of FIG. 2A in accordance with an example embodiment of the disclosure.

FIG. 2B illustrates a cross-sectional view of the example sensor housing assembly 200 of FIG. 2A. FIG. 2B shows a first end 208 and a second end 210 of sensor housing 116, and a sealing channel 212 that extends from the upper external surface 202, of first end 208 of sensor housing 116, to a sensor wire channel 214 (shown with a portion of a sensor disposed therein). FIG. 2B further shows an introducer seal O-ring 216, and a sensor housing seal O-ring 218. Sensor housing 116, introducer 108, insertion shaft cover 106, together with introducer seal O-ring 216, and sensor housing seal O-ring 218, form a sealed region 220 that includes the insertion shaft opening of sensor housing 116 and an inner region of insertion shaft cover 106. Components within the sealed region 220 may be sterilized (e.g., as a separate unit apart from any electrical circuitry on substrate 110 of sensor housing module 100). In some embodiments, sterilization of the sealed region 220 may be achieved by, but is not limited to, exposure to one or more electron or gamma beams. In some embodiments, sealing material such as silicone may be provided into sealing channel 212 to seal around a sensor positioned within the sensor wire channel 214 of the sensor housing 116.

Figure 2C:
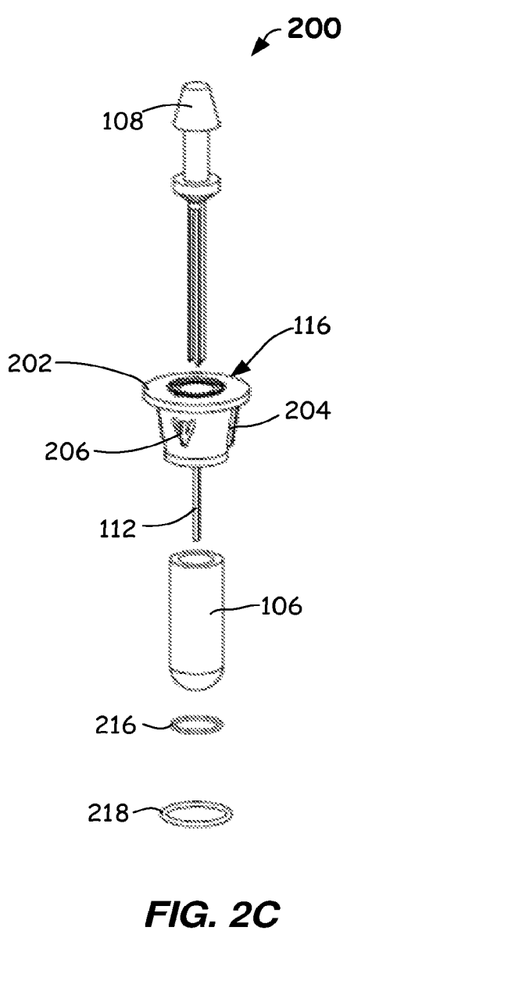
FIG. 2C illustrates an exploded view of the sensor housing assembly of FIG. 2A in accordance with an example embodiment of the disclosure.

FIG. 2C illustrates an exploded view of the example sensor housing assembly 200 of FIG. 2A, including introducer 108, sensor housing 116, sensor 112, insertion shaft cover 106, introducer seal O-ring 216, and sensor housing seal O-ring 218. In some embodiments, introducer seal O-ring 216 and/or sensor housing seal O-ring 218 may be made from a material such as, but not limited to, silicone rubber, buna-N (nitrole) rubber, or fluorosilicone rubber.

As described above, sensor housing 116, introducer 108, insertion shaft cover 106, together with introducer seal O-ring 216, and sensor housing seal O-ring 218, form sealed region 220 (FIG. 2B) that includes the insertion shaft opening of sensor housing 116 and an inner region of insertion shaft cover 106. In some embodiments, sealed region 220 and all components/surfaces therein may be sterilized prior to insertion of sensor housing assembly 200 into bottom case 104 (FIG. 1B). This allows a sterilization method, such as electron- or gamma-beam sterilization, to be used on the components/surfaces within sealed region 220 that would be incompatible with any electrical circuitry present on substrate 110 of bottom case 104. Likewise, the internal region defined by top case 102 and bottom case 104, and any components/surfaces therein such as substrate 110 and electrical circuitry formed thereon, may be sterilized using a method, such as chemical sterilization, that is incompatible with a sensor within sealed region 220 (as described further below).

Figure 3A:
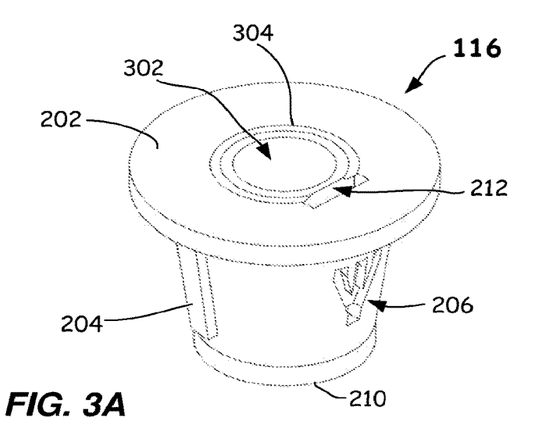
FIG. 3A illustrates a sensor housing in accordance with an example embodiment of the disclosure.

FIG. 3A illustrates an example embodiment of sensor housing 116 in accordance with an embodiment of the disclosure. FIG. 3A shows an insertion shaft opening 302 in sensor housing 116 from the perspective of the top surface 202 of sensor housing 116. FIG. 3A further shows a recess 304 in top surface 202 of sensor housing 116. Recess 304 may be used to receive introducer seal O-ring 216.

Figure 3B:
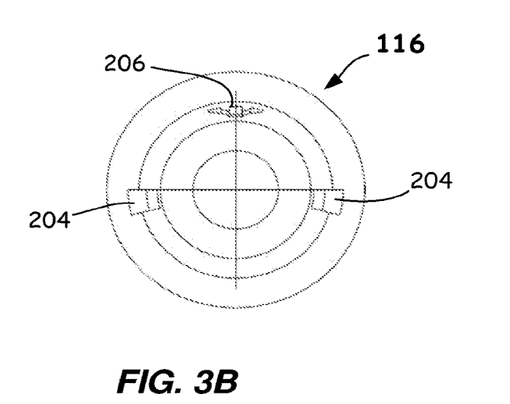
FIG. 3B illustrates a bottom view of the sensor housing of FIG. 3A in accordance with an example embodiment of the disclosure.

FIG. 3B illustrates a bottom view of sensor housing 116 in accordance with an example embodiment of the disclosure. In this view multiple alignment features 204 can be seen, along with sensor wire contact location 206.

Figure 3C:
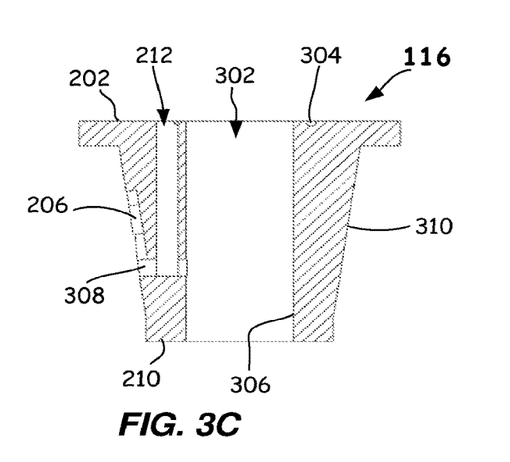
FIG. 3C illustrates a cross-sectional view of the sensor housing of FIG. 3A in accordance with an example embodiment of the disclosure.

FIG. 3C illustrates a cross-sectional view of the sensor housing 116 of FIG. 3A in accordance with an example embodiment of the disclosure. Insertion shaft opening 302 is shown extending through sensor housing 116 from the top surface 202 of sensor housing 116, to the bottom surface 210 of sensor housing 116. A cross-sectional view of recess 304, which is configured to receive an introducer seal O-ring, is shown.

Insertion shaft opening 302 defines an inner surface 306 of sensor housing 116. A sensor wire channel 308 extends through sensor housing 116, from inner surface 306, to an outer surface 310 of sensor housing 116. In this example embodiment, sensor housing 116 is tapered such that it is wider at its top portion, for example, upper external surface 202, than at its bottom portion, for example, bottom surface 210.

Figure 4:
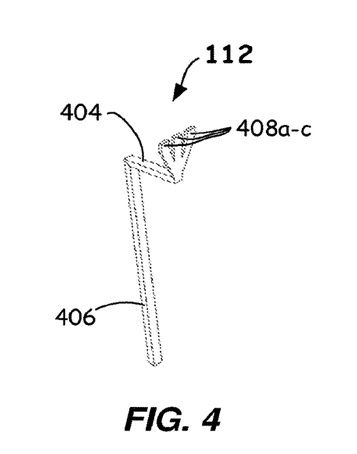
FIG. 4 illustrates a sensor in accordance with an example embodiment of the disclosure.

FIG. 4 illustrates a sensor 112 in accordance with an example embodiment of the disclosure. Sensor 112 may be made from one or more sheets, including a substrate layer such as a vinyl polymer with subsequent layers of gold, silver chloride, and/or various coatings and enzymes suitable for the sensor's use in determining blood glucose levels. Other sensor materials may be used. Sensor 112 includes a first portion 404 and a second portion 406. First portion 404 and second portion 406 are configured to be nominally perpendicular to each in this example embodiment. It will be appreciated that first portion 404 and second portion 406 may be configured to be at a different angular relationship with respect to each other.

Sensor 112 includes fingers 408a-c (also referred to as sensor leads). In this example embodiment, fingers 408a-c are configured to extend from first portion 404 at an angle that allows fingers 408a-c to approximately match the taper of outer surface 310 of sensor housing 116, when first portion 404 of sensor 112 is positioned within sensor wire channel 308 of sensor housing 116, for example. It will be appreciated that any number of sensor fingers may be used, depending on the type of sensor employed. With respect to sensor 112, there is electrical continuity between first portion 404 and second portion 406, and there is electrical continuity between first portion 404 and fingers 408a-c. In some embodiments, sensor 112 may have a diameter of about 250 micrometers to about 500 micrometers for a round sensor, or dimensions of about 250 micrometers$^2$ to about 500 micrometers$^2$ for a square sensor. Other sensor sizes and/or shapes may be used.

Referring to both FIGS. 3C and 4, it can be seen that in this example embodiment, first portion 404 of sensor 112 may be disposed in sensor wire channel 308. Second portion 406 of sensor 112 may be disposed such that it extends through at least a portion of insertion shaft opening 302. Fingers 408a-c of sensor 112 may be disposed in and/or at sensor wire contact location 206. It will be appreciated that the shape and dimensions of sensor wire contact location 206 are configured to accommodate the shape and dimensions of fingers 408a-c of sensor 112, for example.

Figure 5A:
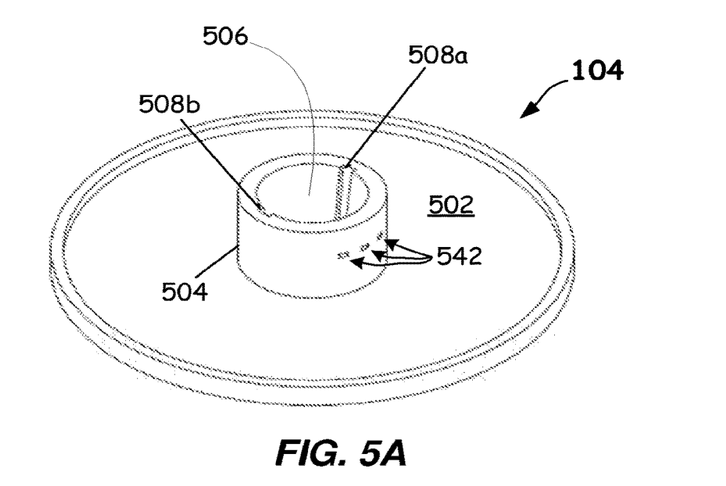
FIG. 5A illustrates a bottom case for a sensor assembly in accordance with an example embodiment of the disclosure.

FIG. 5A illustrates a perspective view of a receiving surface (e.g., bottom case 104) for a sensor assembly in accordance with an example embodiment of the disclosure. Bottom case 104 includes a receiving area 502 configured to receive and support a substrate such as, for example, a circuit board (labeled as substrate 110 in FIG. 5B). Bottom case 104 further includes a sensor housing support 504 that extends upwardly from bottom case 104. Sensor housing support 504 includes sensor housing support opening 506, which is configured to receive sensor housing 116. Sensor housing support 504 further includes alignment slots 508a, 508b, that are configured to slidably engage with corresponding alignment features 204 of sensor housing 116 when sensor housing 116 is received by sensor housing support 504. It will be appreciated that in alternative embodiments, alignment slots may be used on sensor housing 116, and alignment features such as tabs may be used on sensor housing support 504. The purpose of the respective alignment features of sensor housing 116 and sensor housing support 504 is to place sensor housing 116 into a predetermined position relative to the sensor housing support 504. In this way, the electrical connections between sensor 112 and electrical circuitry on substrate 110 can be properly aligned, as described further below. In this example embodiment, sensor housing support 504 may be nominally cylindrical at its outer surface, and sensor housing support opening 506 may have a diameter at an upper portion thereof that is greater than a diameter of sensor housing support opening 506 at a lower portion thereof. In this way, the surface defined by sensor housing support opening 506 may match the outer surface 310 and tapered shape, including alignment features, of sensor housing 116.

In some embodiments, sensor housing support 504 may have a height of about 2.5 mm to 7 mm and an outside diameter of about 4.5 mm to 8.5 mm. Sensor housing 116 may have an outer diameter that tapers from about 5 mm to 4 mm, an inner diameter that ranges from about 1.5 mm to 2 mm, and an overall height of about 5 mm to 7 mm. Other sensor housing support and/or sensor housing dimensions may be used. For example, the outer surface of the sensor housing 116 may have a taper at an angle of about 70 degrees to 85 degrees from horizontal. As shown in FIG. 5C (and FIG. 6C), the mating interface between the sensor housing support 504 and the sensor housing 116 provides a reliable and compact assembly having uniform hoop stress.

Figure 5B:
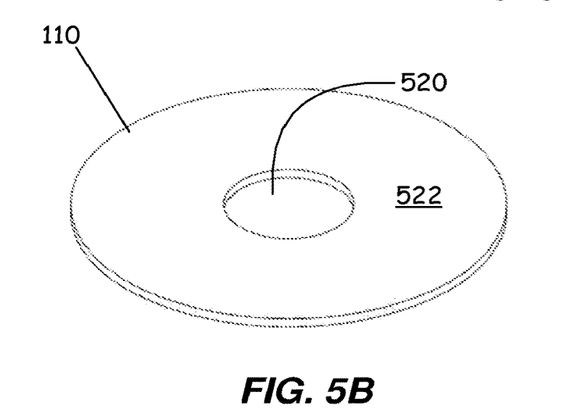
FIG. 5B illustrates a substrate for a sensor assembly in accordance with an example embodiment of the disclosure.
Figure 5C:
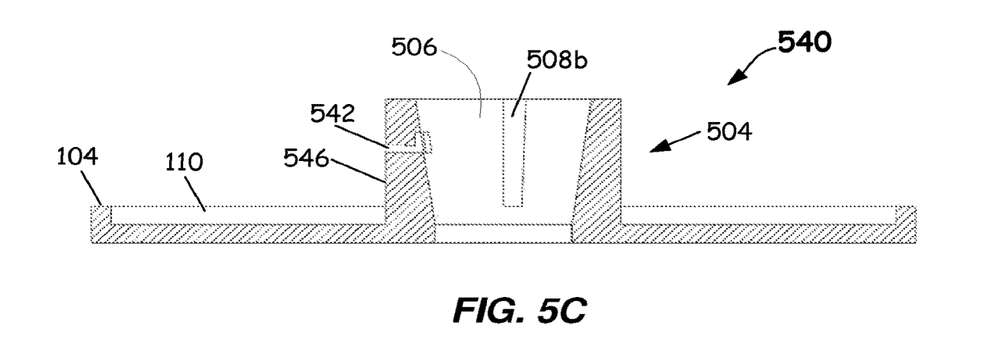
FIG. 5C illustrates a cross-sectional view of the bottom case of FIG. 5A in accordance with an example embodiment of the disclosure.

FIG. 5B illustrates a substrate 110 for a sensor assembly in accordance with an example embodiment of the disclosure. In this example embodiment, substrate 110 may be a circuit board having a circular periphery, and a circular opening 520 centered therein. In this example embodiment, a surface area 522 of substrate 110 is an annular region defined by the diameter of substrate 110 and the diameter of circular opening 520. Circular opening 520 is configured to be of a size such that sensor housing support 504 may pass through circular opening 520 when substrate 110 is disposed in receiving area 502 of bottom case 104.

FIG. 5C illustrates a cross-sectional view of a bottom case and substrate subassembly 540 in accordance with an example embodiment of the disclosure. FIG. 5C shows bottom case 104 having sensor housing support 504 extending upwardly therefrom, and a substrate 110 disposed therein. FIG. 5C further shows sensor housing support 504 having sensor housing support opening 506, and alignment slot 508b. A vertical contact element channel 542 is shown extending through sensor housing support 504 from the sensor housing support opening 506 to an outer surface 546 of sensor housing support 504. In some embodiments, bottom case and substrate subassembly 540 may have an outside diameter of about 15 mm to 40 mm. Other dimensions may be used.

Figure 5D:
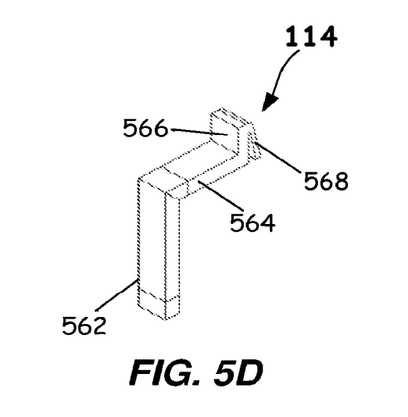
FIG. 5D illustrates a vertical contact element in accordance with an example embodiment of the disclosure.

FIG. 5D illustrates a vertical contact element 114 in accordance with an example embodiment of the disclosure. In this example embodiment, vertical contact element 114 has a first portion 562, a second portion 564, a third portion 566, and a fourth portion 568. First portion 562 extends in a first direction, and is configured to be disposed adjacent outer surface 546 of sensor housing support 504. First portion 562 may have a length configured to extend from an electrically conductive material disposed on substrate 110 to vertical contact element channel 542. Second portion 564 may be nominally perpendicular to first portion 562 in some embodiments, and may have a length configured to extend through vertical contact element channel 542. In some embodiments, third portion 566 may be nominally perpendicular to second portion 564, and fourth portion 568 may extend downwardly at an acute angle from third portion 566. Fourth portion 568 is configured to make electrical contact with one of fingers 408a-c of sensor 112, when sensor housing 116 is received by sensor housing support 504. In general, three vertical contact elements may be provided for making electrical contact between each finger 408a-c of sensor 112 and substrate 110. (Three vertical contact element channels 542 are shown in FIG. 5A, for example.) Other numbers of vertical contact elements may be used. In some embodiments, vertical contact element 114 may be made from high grade stainless steel, solid silver, gold, or copper with a silver/gold/stainless steel plating. In still further embodiments, vertical contact element 114 may be made from a combination of carbon rubber and solid gold/silver to provide a non-bimetal contact. Other vertical contact element materials may be employed. Example widths for vertical contact element 114 range from about 0.4 mm to 1.0 mm. Other vertical contact element dimensions may be used.

Figure 6A:
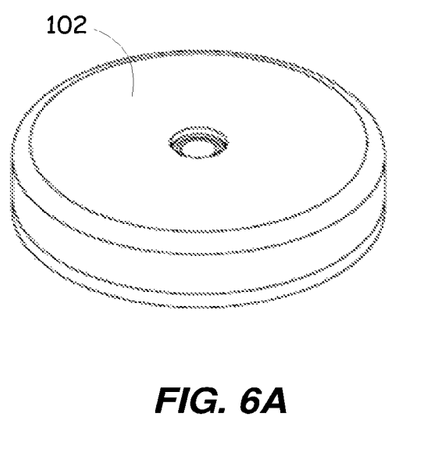
FIG. 6A illustrates a top perspective view of a portion of a sensor assembly in accordance with an example embodiment of the disclosure.
Figure 6B:
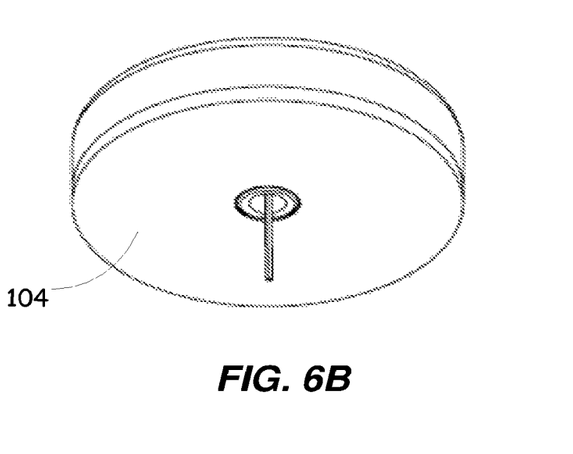
FIG. 6B illustrates a bottom perspective view of a portion of a sensor assembly in accordance with an example embodiment of the disclosure.

FIG. 6A illustrates a top perspective view of a portion of a sensor assembly showing a top case 102 for the sensor assembly in accordance with an example embodiment of the disclosure. FIG. 6B illustrates a bottom perspective view of a portion of a sensor assembly showing a bottom case 104 for the sensor assembly in accordance with an example embodiment of the disclosure.

Figure 6C:
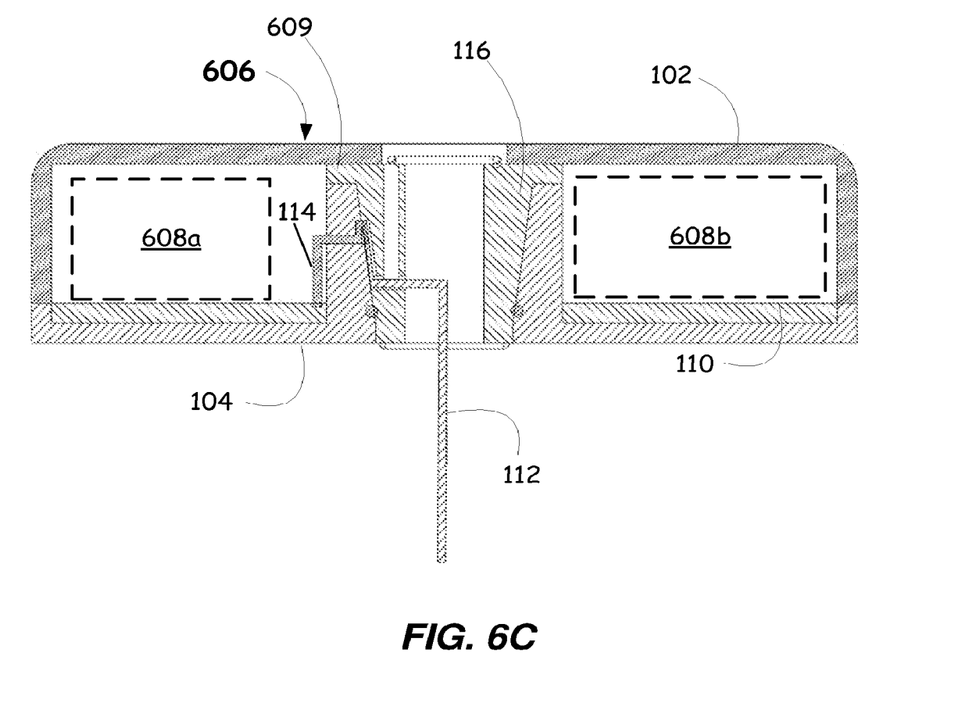
FIG. 6C illustrates a cross-sectional view of a portion of a sensor assembly in accordance with an example embodiment of the disclosure.

FIG. 6C illustrates a cross-sectional view of a portion of a sensor assembly 606 in accordance with an example embodiment of the disclosure (e.g., as the sensor assembly 606 would appear when adhered to a user). In this example embodiment, top case 102 and bottom case 104 are joined so as to enclose substrate 110 and sensor housing 116. Vertical contact element 114 is also enclosed by top case 102 and bottom case 104. FIG. 6C is similar to FIG. 1B, but the insertion shaft and insertion shaft cover are absent from this view in order to clearly illustrate the relationship between sensor 112 and vertical contact element 114. It can be seen here that when sensor housing 116 is received by sensor housing support 504, in an aligned manner as prescribed by the alignment features 204 of sensor housing 116 and the corresponding alignment slots 508a-b of sensor housing support 504, that sensor 112 makes electrical contact with each vertical contact element 114. (A different vertical contact element 114 may contact a different one of fingers 408a-c.) In some embodiments, sensor housing 116 may have an outer flange 609 that rests on top of sensor housing support 504 when sensor housing 116 is positioned within sensor housing support 504.

As further shown in FIG. 6C, electrical circuitry 608a and/or 608b may be electrically connected and/or supported by substrate 110 (e.g., a circuit board). Example electrical circuitry 608a and 608b may include, for example, one or more processors, memory, a battery, a transmitter and/or receiver for communicating information to and/or receiving information from an external device, or the like. Sensor 112 may make electrical contact to electrical circuitry 608a and/or 608b through vertical contact elements 114. In some embodiments, top case 102 and bottom case 104 may form a sealed internal environment that is isolated from sensor 112.

Figure 7:
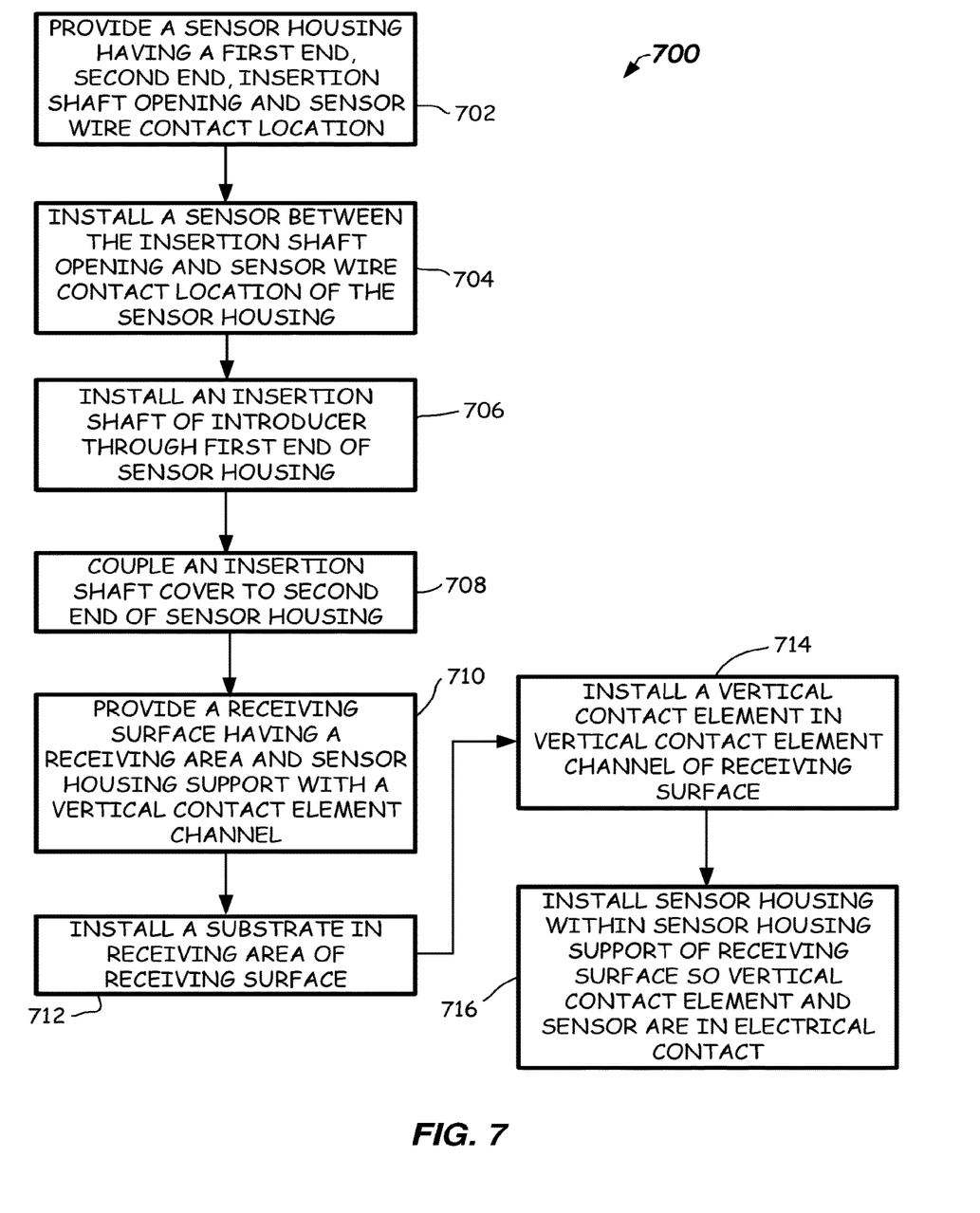
FIG. 7 illustrates a flow diagram of a method of assembling a sensor assembly for a continuous glucose monitoring system in accordance with an example embodiment of the disclosure.

Referring to FIG. 7, a flow diagram of an example method 700 of assembling a sensor assembly for a continuous glucose monitoring system in accordance with an embodiment of the disclosure is provided. In this example embodiment, at a block 702, a sensor housing having a first end, a second end, an insertion shaft opening, and a sensor wire contact location may be provided. The first end may have a sealing surface configured to seal against an introducer (having an insertion shaft), and the second end may have a sealing surface configured to seal against an insertion shaft cover. The insertion shaft opening may extend between the first end and the second end, and have a width that allows at least a portion of the insertion shaft to travel through the insertion shaft opening. The insertion shaft opening may define an inner surface of the sensor housing. The sensor wire contact location may be formed in an outer surface of the sensor housing.

At a block 704, a sensor may be installed between the insertion shaft opening and the sensor wire contact location of the sensor housing. (Note that in some embodiments the sensor may be installed with the insertion shaft in block 706.) At a block 706, an insertion shaft may be installed through the first end of the sensor housing. For example, an introducer having an insertion shaft may be placed in sealing contact with the sensor housing using one or more sealing members (e.g., introducer seal O-ring 216 in FIG. 2B).

At a block 708, an insertion shaft cover may be coupled to the second end of the sensor housing. For example, as shown in FIG. 2B, sensor housing seal O-ring 218 may seal insertion shaft cover 106 to sensor housing 116. Sensor housing 116, introducer 108, insertion shaft cover 106, together with introducer seal O-ring 216, and sensor housing seal O-ring 218, form a sealed region 220 that includes the insertion shaft opening of sensor housing 116 and an inner region of insertion shaft cover 106. Components within the sealed region 220 may be sterilized (e.g., as a separate unit apart from any electrical circuitry on substrate 110 of sensor housing module 100). In some embodiments, introducer seal O-ring 216 and/or sensor housing seal O-ring 218 may be made from a material such as, but not limited to, silicone rubber, buna-N (nitrole) rubber, or fluorosilicone rubber.

At a block 710, a receiving surface, such as a bottom case or other receiving surface, having a receiving area and a sensor housing support with a vertical contact element channel is provided. At a block 712, a substrate such as a circuit board may be installed in the receiving area of the receiving surface. The substrate may be a laminated circuit board, a flex circuit, a flex printed circuit board, or any other suitable substrate for positioning and/or interconnecting electronic circuitry (e.g., one or more insulating or dielectric materials with electrical conductors for connecting circuitry). Circuitry is disposed on, and/or in, the substrate. Circuitry may include circuits housed in packages that are mounted directly to the substrate, and/or coupled to corresponding sockets, which are attached to the substrate. At a block 714, a vertical contact element may be installed in the vertical contact element channel of the receiving surface. At a block 716, the sensor housing is installed within the sensor housing support of the receiving surface such that the vertical contact element and the sensor are in electrical contact with each other. An adhesive may be applied to the bottom of the receiving surface (e.g., a bottom case). For example, the adhesive may include an adhesive strip or ring, having a protective film that is removable prior to placement of the bottom case on the skin of a user. Example adhesives include silicone-based adhesives, acrylic adhesives, polyisobutylene adhesives, or the like.

Figure 8:
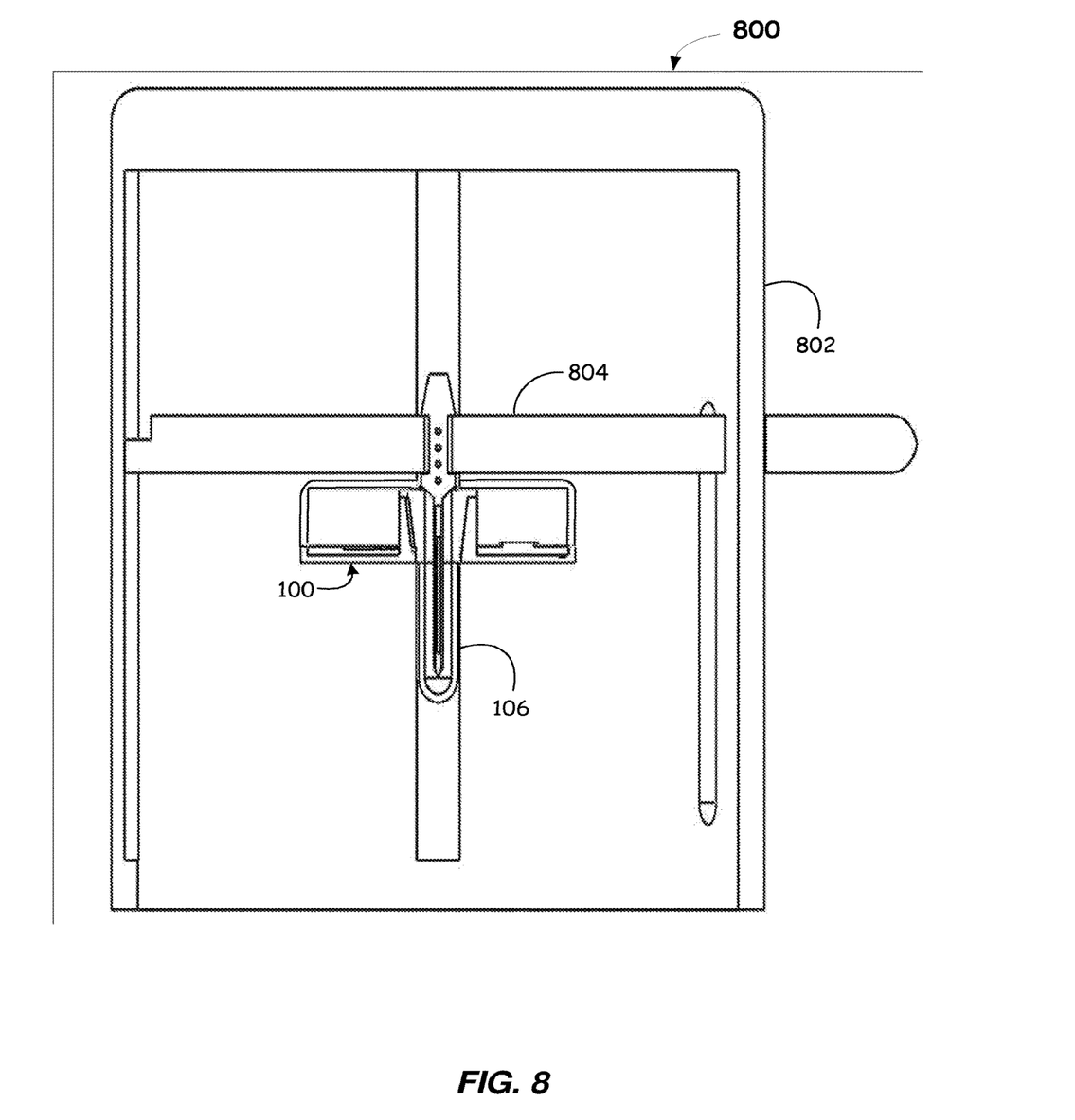
FIG. 8 illustrates a cross-sectional view of an assembly that includes a sensor housing module within a sensor applicator prior to insertion of the sensor through a patient's skin.

FIG. 8 illustrates a cross-sectional view of a sensor applicator 800 prior to its use for inserting a sensor into a patient. Sensor applicator 800 may include a sensor housing module 100 within a sensor applicator body 802. In this example embodiment, prior to insertion of the sensor through a patient's skin, the entirety of sensor housing module 100 is within sensor applicator body 802. Assembly 800 further includes a member 804 that may be horizontally oriented with respect to sensor housing module 100, and configured to engage with sensor housing module 100 so as to apply a downward force during an insertion process that inserts a sensor into a patient's skin. A portion of member 804 may extend laterally through an opening in sensor applicator body 802 such that a patient, or other user, may access that portion of member 804. In operation, after removal of insertion shaft cover 106, a patient, or other user, applies a downward force to that portion of member 804 that is outside of sensor applicator body 802, to insert a sensor into the patient. The sensor applicator 800 may also be referred to as a sensor inserter.

Figure 9:
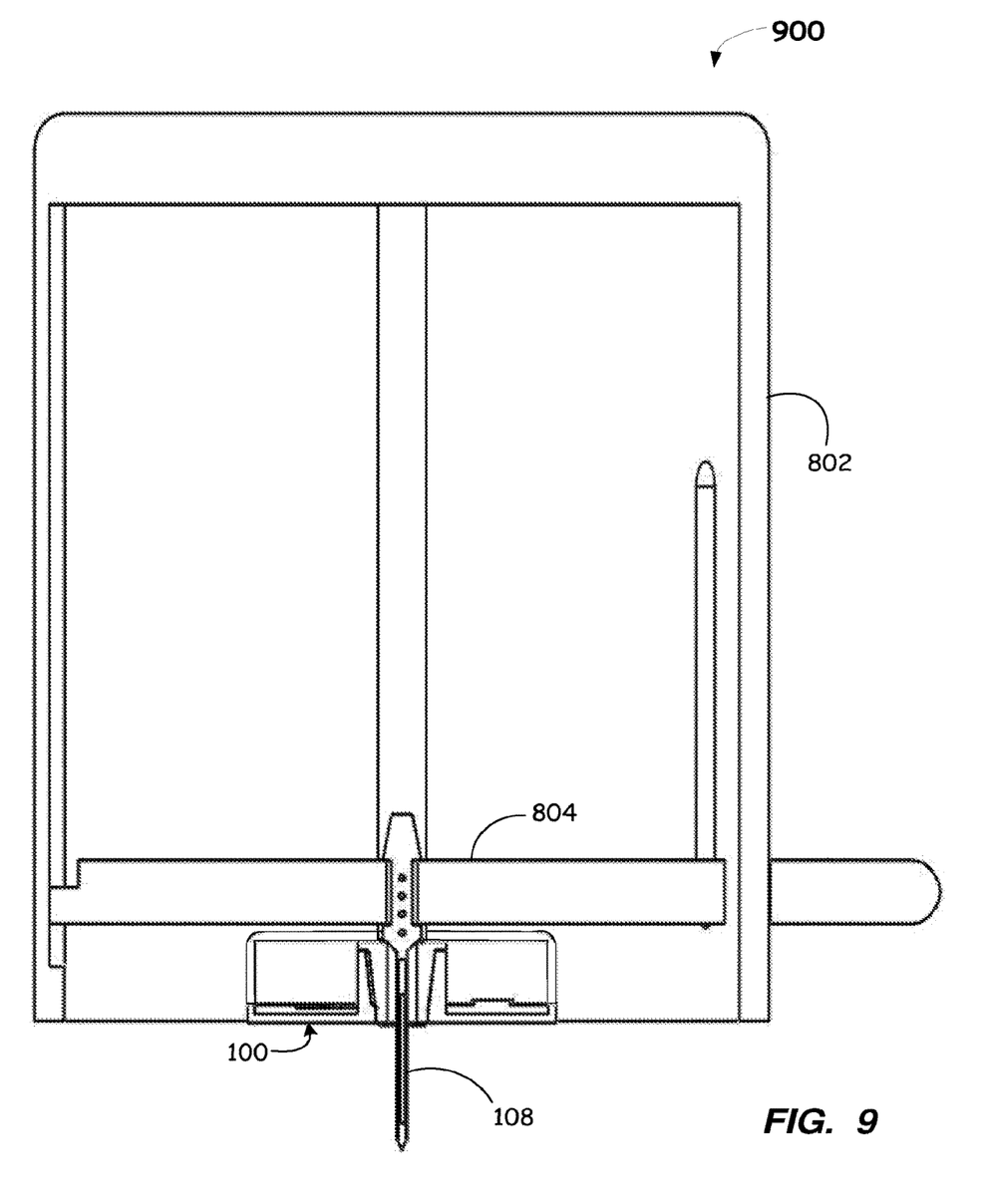
FIG. 9 illustrates a cross-sectional view of an assembly that includes a sensor housing module within a sensor applicator subsequent to removal of an insertion shaft cover and movement of the insertion shaft into the insertion position for inserting the sensor through a patient's skin.

FIG. 9 illustrates a cross-sectional view of an assembly 900 subsequent to its use for inserting a sensor into a patient. Assembly 900 includes sensor housing module 100 within a sensor applicator 802 subsequent to removal of insertion shaft cover 106, and movement of the introducer 108 to the insertion position for inserting the sensor through a patient's skin.

While described primarily with regard to continuous glucose monitoring, it will be understood that the vertical contact arrangements and/or separately sterilizable regions described herein, such as the sensor housing, sensor housing assemblies, and/or sensor housing modules of FIGS. 1A-9, may be employed in other monitoring applications to monitor other body fluid levels such as cholesterol, Hb1AC, ketones, PH, oxygen saturation, etc.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a smartphone," does not imply that any or all of the three items of that list are mutually exclusive and does not imply that any or all of the three items of that list are comprehensive of any category.

A description of an embodiment with several components or features does not imply that all or even any of such components and/or features are required. On the contrary, a variety of optional components are described to illustrate the wide variety of possible embodiments in accordance with this disclosure. Unless otherwise specified explicitly, no component and/or feature is essential or required.

When an ordinal number (such as "first," "second," "third," and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget." Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

The foregoing description discloses only example embodiments. Modifications of the above-disclosed apparatus and methods which fall within the scope of this disclosure will be readily apparent to those of ordinary skill in the art.

What is claimed is:

1. A method of assembling a continuous monitoring apparatus comprising a sensor housing assembly and a bottom case, the method comprising:
    assembling the sensor housing assembly, comprising:
        providing a sensor housing comprising a first end and a second end with an insertion shaft opening disposed therebetween,
            wherein the insertion shaft opening defines an inner surface and an outer surface having a sensor wire contact location disposed on the outer surface,
            wherein a sensor wire channel extends between the inner surface and the sensor wire contact location; and
        installing a sensor such that the sensor extends through the sensor wire channel with a first portion of the sensor disposed in the insertion shaft opening and a second portion of the sensor disposed at the sensor wire contact location;
    assembling the bottom case, comprising:
        providing a receiving surface with a sensor housing support extending therefrom,
            wherein the sensor housing support defines an inner wall and an outer wall with a vertical contact element channel extending therethrough;
        installing a substrate to the receiving surface, the substrate having an electrical circuitry coupled thereto; and
        installing a vertical contact element within the vertical contact element channel; and
    installing the sensor housing assembly within the sensor housing support,
        wherein the second portion of the sensor contacts the vertical contact element and forms an electrical connection with the vertical contact element upon installing the sensor housing assembly within the sensor housing support,
        wherein the vertical contact element is electrically coupled to the electrical circuitry prior to contacting the sensor,
        wherein contact of the second portion of the sensor with the vertical contact element makes electrical contact of the sensor to the electrical circuitry, the contact occurring externally to the sensor housing.

2. The method of claim 1, wherein installing the vertical contact element further comprises placing a first end of the vertical contact element at the outer wall of the sensor housing support and placing a second end of the vertical contact element at the inner wall of the sensor housing support.

3. The method of claim 2, further comprising:
    aligning the second portion of the sensor and the second end of the vertical contact element via an alignment feature disposed at one or more of the outer surface of the insertion shaft opening or the inner wall of the sensor housing support.

4. The method of claim 3, wherein the first end of the vertical contact element is substantially parallel with the outer wall of the sensor housing support.

5. The method of claim 4, wherein the sensor housing includes a sealing channel extending from the first end of the sensor housing to the sensor wire channel, and further comprising:
    introducing a sealing material in the sealing channel to seal around the sensor positioned within the sensor wire channel.

6. The method of claim 5, further comprising:
    inserting an introducer through the insertion shaft opening, the introducer comprising a handle portion arranged to seal the insertion shaft opening at the first end and an insertion shaft extending beyond the second end of the sensor housing.

7. The method of claim 6, further comprising:
    prior to installing the sensor housing assembly within the sensor housing support, sterilizing the sensor housing assembly using one or more of an electron beam or a gamma beam.

8. The method of claim 7, further comprising:
    prior to installing the sensor housing assembly within the sensor housing support, sterilizing the bottom case using chemical sterilization.

9. The method of claim 8, further comprising:
    attaching an insertion shaft cover to the second end of the sensor housing, the insertion shaft cover protecting the first portion of the sensor and the insertion shaft extending beyond the second end of the sensor housing.

10. The method of claim 1,
    wherein the vertical contact element comprises a first portion that contacts the electrical circuitry on the substrate and a second portion that extends through the vertical contact element channel,
    wherein the first portion of the vertical contact element is perpendicular to the second portion of the vertical contact element and the vertical contact element channel.

* * * * *